United States Patent
Plos

(10) Patent No.: US 7,527,654 B2
(45) Date of Patent: May 5, 2009

(54) DYEING PROCESS USING A DYE OF STYRYL OR IMINE TYPE IN COMBINATION WITH A WEAK ACID, AND DEVICE FOR IMPLEMENTING THE PROCESS

(75) Inventor: Grégory Plos, Tokyo (JP)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/907,525

(22) Filed: Oct. 12, 2007

(65) Prior Publication Data

US 2008/0189878 A1 Aug. 14, 2008

Related U.S. Application Data

(60) Provisional application No. 60/853,757, filed on Oct. 24, 2006.

(51) Int. Cl.
*A61Q 5/10* (2006.01)
*C07D 279/00* (2006.01)
*C07D 265/00* (2006.01)

(52) U.S. Cl. .................. 8/405; 8/426; 8/435; 8/565; 8/570; 8/571; 8/572; 8/575; 132/202; 132/208; 540/546; 544/89

(58) Field of Classification Search .......... 8/405, 8/426, 435, 565, 570, 571, 572, 575; 132/202, 132/208; 540/546; 544/89
See application file for complete search history.

(56) References Cited

U.S. PATENT DOCUMENTS

| | | | |
|---|---|---|---|
| 4,003,633 A | 1/1977 | Yamashita | |
| 4,139,274 A | 2/1979 | Yamashita et al. | |
| 4,147,862 A | 4/1979 | Hayami et al. | |
| 4,314,058 A * | 2/1982 | Hayami et al. | 544/89 |
| 4,340,624 A | 7/1982 | Yamashita et al. | |
| 4,380,629 A | 4/1983 | Yamashita et al. | |
| 7,399,319 B2 | 7/2008 | Plos | |
| 2006/0182697 A1 | 8/2006 | Lalleman et al. | |

FOREIGN PATENT DOCUMENTS

| | | |
|---|---|---|
| DE | 2 541 665 | 4/1976 |
| EP | 1 747 774 | 1/2007 |
| FR | 2 285 438 | 4/1976 |
| FR | 2 285 439 | 4/1976 |
| FR | 2 293 024 | 6/1976 |
| FR | 2 888 747 | 1/2007 |
| JP | 55-031057 | 3/1980 |
| JP | 55-113710 | 9/1980 |
| JP | 57-014652 | 1/1981 |
| JP | 56-025106 | 3/1981 |
| JP | 56-081522 | 7/1981 |
| JP | 56-150006 | 11/1981 |
| JP | 56-161489 | 12/1981 |
| JP | 58-048031 | 3/1983 |
| JP | 59-121319 | 7/1984 |
| JP | 59-052193 | 12/1984 |
| JP | 60-057320 | 4/1985 |
| JP | 60-057322 | 4/1985 |
| JP | 60-057323 | 4/1985 |
| JP | 60-200233 | 10/1985 |
| JP | 61-121040 | 6/1986 |
| JP | 61-147235 | 7/1986 |
| JP | 63-280727 | 11/1988 |
| JP | 02-179618 | 7/1990 |
| JP | 08-222268 | 8/1996 |
| JP | 10-114151 | 5/1998 |
| JP | 11-034489 | 2/1999 |
| JP | 11-034497 | 2/1999 |
| JP | 2000-292817 | 10/2000 |
| JP | 2001-081342 | 3/2001 |
| JP | 2001-109021 | 4/2001 |
| JP | 2001-246862 | 9/2001 |
| JP | 2003-315839 | 11/2003 |

OTHER PUBLICATIONS

STIC Search Report dated Aug. 14, 2008.*
"Sciences des traitements capillaires" by Charles Zviak, 1988, published by Masson, pp. 215 and 278.
Biochemistry text by J .H. Weil, 1983, p. 5 et seq.
Biochemistry text by Lubert Stryer, 1995, p. 22.
Biochemistry text by A. Lehninger, 1993, pp. 115-116.
French Search Report issued in French Patent Application No. FR 0 654 259 (Oct. 13, 2006).
International Search Report issued in International Patent Application No. PCT/FR2007/052129 (2007).

* cited by examiner

*Primary Examiner*—Eisa B Elhilo
(74) *Attorney, Agent, or Firm*—Finnegan, Henderson, Farabow, Garrett & Dunner, LLP

(57) ABSTRACT

The present invention relates to a process for dyeing keratin fibers, in particular human keratin fibers such as the hair, using a dye composition comprising at least one dye of styryl or imine type in the presence of a revealing composition comprising at least one optionally substituted (hetero) aromatic compound of weak acid type. The present invention makes it possible in particular to obtain a chromatic and fast coloration of keratin fibers, which is visible even on dark hair without prior lightening. The invention also makes it possible to obtain a coloration which, under certain conditions, does not stain.

24 Claims, No Drawings

DYEING PROCESS USING A DYE OF STYRYL OR IMINE TYPE IN COMBINATION WITH A WEAK ACID, AND DEVICE FOR IMPLEMENTING THE PROCESS

CROSS-REFERENCE TO RELATED APPLICATIONS

This application claims benefit of priority under 35 U.S.C. § 119 to French Patent Application No. 0654259, filed Oct. 13, 2006, and the benefit of U.S. Provisional Application No. 60/853,757, filed Oct. 24, 2006, the content of all which is incorporated herein by reference.

FIELD OF THE INVENTION

The present invention relates to a process for dyeing keratin fibres, in particular human keratin fibres such as the hair, using a dye composition comprising at least one dye of styryl or imine type in the presence of a revealing composition comprising at least one compound of weak acid type. The invention also relates to a device suitable for implementing said process.

BACKGROUND OF THE INVENTION

It is known practice to dye keratin fibres, and in particular human keratin fibres such as the hair, with dye compositions containing oxidation dye precursors, which are generally known as oxidation bases, such as ortho- or para-phenylene-diamines, ortho- or para-amino-phenols and heterocyclic compounds such as diamino-pyrazole derivatives. These oxidation bases are colourless or weakly coloured compounds which, when combined with oxidizing products, give rise to coloured compounds by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds such as indole compounds.

Another advantage of this type of dyeing is that it is visible on dark hair. Effectively, since the oxidative process is performed in an alkaline medium, most generally in the presence of aqueous ammonia, the bleaching of melanin, the natural pigment of keratin fibres and especially of the hair, takes place in parallel with the condensation of the dye precursors. The colour obtained may thus also be visible even on dark hair.

The colorations obtained show good fastness in particular with respect to shampooing. However, it is rare to be able to obtain chromatic colorations via this method.

It is also known practice to dye keratin fibres with compositions containing direct dyes. These compounds are coloured and colouring molecules with affinity for keratin fibres. They are applied to the fibres for a period of time necessary to obtain the desired coloration, and are then generally rinsed out.

The standard direct dyes used are in particular dyes of the nitrobenzene, anthraquinone, nitropyridine, azo, cationic azo, xanthene, acridine, azine or triaryl-methane type or natural dyes.

It is possible to obtain colorations that are lighter than those of the hair before dyeing, if the direct dyeing is carried out in the presence of an oxidizing agent. This is then referred to as direct dyeing under lightening conditions.

Direct dyeing advantageously makes it possible to achieve very chromatic colours, but they always have the drawback of being temporary or semi-permanent. In fact, the fastness of direct dyes on the hair remains limited, which leads to fading of the colour, or even to the colour changing over time, due to loss of one or more of the dyes used.

One drawback of these two dyeing modes is the need to use an oxidizing composition for the oxidation dyeing or to obtain lightened direct dyeing. It is known that oxidizing compositions, in the long run, cause degradation of hair fibres.

Another drawback of these two dyeing modes lies in the fact that the compositions are initially coloured, as in the case of dye compositions using direct dyes, or else they become coloured during the application, as is the case of compositions comprising one or more oxidation dye precursors. Consequently, direct dyeing and oxidation dyeing have the drawback of being soiling.

French Application FR 05 52277 has recently described the use of compounds of styryl or imine type existing in a coloured form and in a colourless form, for dyeing keratin fibres. Thus, under certain conditions, the composition used is colourless or weakly coloured and the colour is revealed in the keratin fibres once the composition has been applied, which makes it possible to solve the problem of staining of the skin and of the fabrics used.

Although these compositions afford many advantages over the existing compositions, while at the same time offering satisfactory dyeing efficacy, it nevertheless. remains that it may be desired to further increase the uptake and to reduce the selectivity of the coloration obtained.

SUMMARY OF THE INVENTION

The aim of the present invention is thus to propose a process for dyeing keratin fibres that does not have the drawbacks of the known processes. In particular, one of the aims of the present invention is to propose processes for obtaining chromatic, strong colorations that are fast, especially with respect to shampooing.

The present invention also allows access to keratin fibre colorations that are lighter than the initial colour, without necessarily using an oxidizing composition.

Finally, the process according to the invention makes it possible, under certain conditions, to propose a process that does not stain.

DETAILED DESCRIPTION OF THE INVENTION

These aims and others are achieved by the present invention, a subject of which is a process for dyeing keratin fibres, consisting in bringing said fibres into contact with a dye composition comprising, in a suitable dyeing medium, at least one compound of formula (I), and the addition salts thereof:

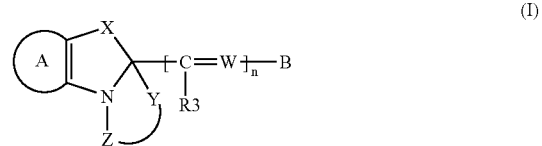

(I)

in which:

A is a substituted or unsubstituted, 5- to 16-membered, fused or non-fused aromatic or heteroaromatic nucleus;

X represents an oxygen atom, a sulphur atom or a group $CR_1R_2$;

$R_1$ and $R_2$ represent, independently of each other, a hydrogen atom, a $C_1$-$C_6$ alkyl radical, a $C_1$-$C_6$ hydroxyalkyl radical, a $C_1$-$C_6$ alkoxyalkyl radical or an alkylene chain that may contain an oxygen or sulphur atom; $R_1$ and $R_2$ may together form an aromatic or non-aromatic 5- or 6-membered ring optionally containing one or more heteroatoms such as a nitrogen, oxygen or sulphur atom;

$R_3$ represents a hydrogen atom, a halogen atom, a $C_1$-$C_6$ alkyl radical, a cyano radical, an aromatic group, a phenoxy group or a nitro radical;

W represents a group $CR_4$ or a nitrogen atom;

$R_4$ represents a hydrogen atom, a halogen atom, a $C_1$-$C_6$ alkyl radical, a cyano radical, an aromatic group, a phenoxy radical or a nitro radical;

Y represents an oxygen atom, a sulphur atom or a group $NR_5$;

$R_5$ represents a hydrogen atom or a $C_1$-$C_6$ alkyl radical;

Z represents a group —$C_pH_{2p}$—, with p being an integer between 2 and 4, which may be unsubstituted or substituted with one or more substituents chosen from halo, hydroxyl, alkyl, haloalkyl, alkoxy, amino, mono- or dialkylamino, mono- or dihydroxyalkylamino and carboxyl radicals; a group —$C_qH_{2q}CO$—, with q being an integer between 1 and 3, which may be unsubstituted or substituted with one or more substituents chosen from halo, hydroxyl, alkyl, haloalkyl, alkoxy, amino, mono- or dialkylamino, mono- or dihydroxyalkylamino and carboxyl radicals;

n represents an integer from 1 to 4;

B represents a substituted or unsubstituted, 5- to 16-membered, fused or non-fused aromatic or heteroaromatic nucleus, in combination with a revealing composition comprising at least one compound of formula (II) $R_6(R_7CR_8)_n$—COOX, or a precursor of such a compound, in which formula:

$R_6$ represents a fused or non-fused, 5- to 16-membered nucleus of aromatic or heteroaromatic type comprising at least one nitrogen, oxygen or sulphur atom, optionally substituted with one or more hydroxyl, $C_1$-$C_3$ alkoxy, hydroxy-carbonyl, alkoxycarbonyl with the alkoxy group being $C_1$-$C_3$, amino or cyano groups;

n is an integer ranging from 0 to 6;

$R_7$ and $R_8$ represent, independently of each other, a hydrogen atom, a linear or branched, substituted or unsubstituted $C_1$-$C_6$ alkyl group, a hydroxyl group, a $C_1$-$C_6$ methoxy group, a cyano group, an amino group or a hydroxycarbonyl or alkoxycarbonyl group;

X represents a hydrogen atom, a monovalent cation, more particularly such as a cation of an alkali metal such as sodium or potassium, or an ammonium cation.

A subject of the invention is also a multicompartment device, in which one of the compartments contains the compound(s) of formula (I) and another contains the compound(s) of formula (II).

The invention makes it possible in particular to obtain a keratin fibre coloration that is chromatic and fast, in particular with respect to shampooing.

As indicated previously, another advantage of the invention is that of providing a clean method of dyeing, in other words a method that does not stain.

Specifically, under certain conditions of implementation of the invention, the compound applied to the keratin fibres is colourless or weakly coloured and the coloration is not revealed under later, once the compound has been applied to the keratin fibres.

The revelation of the coloration is performed by opening the heterocycle to lead to species of formula (I') below, which are coloured:

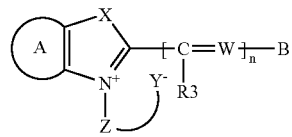

A, X, Z, W, $R_3$ and n having the same meanings as those indicated previously.

The opening of the heterocycle formed by N, Y and Z in the dye compounds of formula (I) may be performed under the effect of a stimulus such as light, an electrical current, heat, the addition of an acidifying agent, the addition of solvent or an electromagnetic radiation.

The dye composition applied to the keratin fibres is therefore substantially colourless, and transparent or non-transparent, as are the rinsing waters or the shampoo-rinsing waters. Thus, the application of the composition according to the invention may be non-soiling.

Moreover, it is possible to efface the colour obtained. It is in fact sufficient to treat the keratin fibres, coloured with the composition according to the invention, with a composition whose role will be to increase the pH of the fibres above the pKa of the dyes of formula (I) present on and in the fibres. The open heterocycles of the compounds of formula (I') will reclose to once again give the compounds of formula (I).

Finally, it has been found that the application of the dye composition to dark hair, more particularly characterized by a tone depth of less than or equal to 6, leads to an increase in the tone depth of the coloration by at least one tone, which corresponds to visible lightening of the fibre, without the need to use an oxidizing composition.

In the context of the present invention, the term "heteroaromatic nucleus" means an aromatic nucleus comprising one or more heteroatoms such as nitrogen, sulphur, oxygen or phosphorus atoms.

In the context of the present invention, the term "fused" means at least two conjoined rings with at least two atoms in common.

A halo radical denotes a halogen atom chosen from chlorine, bromine, iodine and fluorine.

The term "alkyl radical" (alk) means a linear or branched radical, for example a methyl, ethyl, n-propyl, isopropyl, n-butyl or tert-butyl radical. An alkoxy radical is an alk-O— radical, a mono- or dialkylamino radical is a radical —N(alk)$_n$ with n=1 or 2, an alkylcarbonyl radical is an alk-CO— radical, an alkoxycarbonyl radical is an alk-O-CO— radical, and an alkylcarbonylalkyl radical is an alk-CO-alk-radical, in each of these definitions the alkyl radical being as defined above.

A substituted alkyl radical is a monosubstituted or polysubstituted alkyl. For example, a hydroxyalkyl or an aminoalkyl is an alkyl that may be substituted with one or more hydroxyl or amino groups.

The term "aryl radical" (Ar) means a carbon-based radical derived from fused or non-fused benzene compounds, for example phenyl, anthracenyl or naphthyl.

Examples of aromatic or non-aromatic 5- or 6-membered rings that may be mentioned include 1,3-cyclopentadiene, benzene, cyclopentane and cyclobutane.

The compounds of formula (I) may be neutralized with an anionic or cationic counterion when they bear a charge. The negative counterions may be chosen, for example, from a halide such as a chloride, a bromide, an iodide or a fluoride, perchlorate, p-methylbenzenesulphonate, tetrafluoroborate, sulphate, alkyl sulphate, toluene-sulphonate or sulphonate. The cationic counterions may be chosen from the cations derived from alkali metal and alkaline-earth metal salts, such as sodium or potassium ions.

In the context of the present invention, the term "dark hair" means hair whose tone depth is less than or equal to 6 (dark blonde) and preferably less than or equal to 4 (chestnut).

It is recalled that the lightening of the hair is evaluated by the "tone depth", which characterizes the degree or level of lightening. The notion of "tone" is based on the classification of natural shades, one tone separating each shade from the one immediately following or preceding it. This definition and the classification of natural shades are well known to hairstyling professionals and are published in the book "Sciences des traitements capillaires" by Charles Zviak, 1988, published by Masson, pp. 215 and 278. The tone depths range from 1 (black) to 10 (light blond), one unit corresponding to one tone; the higher the figure, the lighter the shade.

According to one particular embodiment of the invention, A in formula (I) is a benzene, anthracene, naphthalene or quinoline nucleus.

According to one particular embodiment of the invention, A is unsubstituted or substituted with one or more groups that may be chosen from a halo radical, a $C_1$-$C_6$ alkyl radical, a $C_1$-$C_6$ alkoxy radical, a $C_1$-$C_6$ alkylsulphonyl radical (—$SO_2$-alkyl), a $C_1$-$C_6$ alkyl-sulphonate radical (—$SO_3$-alkyl), a cyano radical, a trifluoromethyl radical, a $C_1$-$C_6$ alkylcarbonyl radical, a trifluoromethylsulphonyl radical (—$SO_2$—$CF_3$), a tri-fluoromethylcarbonyl radical, a phenylsulphonyl radical (—$SO_2$-Ph), a phenylsulphonate radical (—$SO_2$-Ph), a phenylcarbonyl radical, a nitro radical, a $C_1$-$C_6$ alkoxycarbonyl radical, a phosphonyl radical (—PO(OH)$_2$), a phosphonyl ($C_1$-$C_6$)alkyl radical (-alkyl-PO(OH)$_2$), a hydroxyl radical, an amino radical, a di($C_1$-$C_6$)alkylamino radical, a (hydroxy($C_1$-$C_6$)alkyl)amino radical, a di(hydroxy($C_1$-$C_6$)alkyl)amino radical, an (amino($C_1$-$C_6$)alkyl)amino radical, a di(amino($C_1$-$C_6$)-alkyl)amino radical, a (hydroxy($C_1$-$C_6$)alkyl)()((($C_1$-$C_6$)-alkyl)amino radical, an (amino($C_1$-$C_6$)alkyl)()((($C_1$-$C_6$)-alkyl)amino radical, an (amino($C_1$-$C_6$)alkyl)(hydroxy-($C_1$-$C_6$)alkyl)amino radical, a hydroxy($C_1$-$C_6$)alkyl radical, an amino($C_1$-$C_6$)alkyl radical, a (($C_1$-$C_6$)alkyl)amino($C_1$-$C_6$)alkyl radical, a di(($C_1$-$C_6$)alkyl)-amino ($C_1$-$C_6$) alkyl radical, a (hydroxy($C_1$-$C_6$)alkyl)amino-($C_1$-$C_6$)alkyl radical, a di(hydroxy($C_1$-$C_6$)alkyl)amino-($C_1$-$C_6$) alkyl radical, an (amino($C_1$-$C_6$)alkyl)amino($C_1$-$C_6$)-alkyl radical, a di(amino($C_1$-$C_6$)alkyl)amino($C_1$-$C_6$)alkyl radical, a (($C_1$-$C_6$)alkyl)(hydroxy($C_1$-$C_6$)alkyl)amino-($C_1$-$C_6$)alkyl radical, an (amino($C_1$-$C_6$)alkyl)()((($C_1$-$C_6$)-alkyl)amino radical, a (hydroxy($C_1$-$C_6$)alkyl)()((($C_1$-$C_6$)-alkyl)amino($C_1$-$C_6$) alkyl radical, a phenyl ($C_1$-$C_6$) alkyl radical optionally substituted with one or more substituents chosen from halo, hydroxyl, alkyl, haloalkyl, alkoxy, amino, mono- or dialkylamino, mono- or dihydroxyalkylamino and carboxyl radicals, a cationic group of the quaternary ammonium type, a $C_1$-$C_6$ alkyl radical substituted with a cationic group of the quaternary ammonium type, a carboxyl radical, a ($C_1$-$C_6$) alkyl radical substituted with a carboxyl radical, a thiol radical, a thio($C_1$-$C_6$)alkyl radical, a sulphonate radical (—$SO_3^-$), a ($C_1$-$C_6$)alkyl radical substituted with a sulphonate radical, a ($C_1$-$C_6$)alkylcarbonyl($C_1$-$C_6$)alkyl radical, a di(halo($C_1$-$C_6$)alkyl)amino radical, an acetamido radical, an aryloxy radical, an aryloxy-($C_1$-$C_6$)alkyl radical, an ethenyl radical (—CH═$CH_2$), an ethenylcarbonyl radical (—CO—CH═$CH_2$); two adjacent groups possibly forming an aromatic or heteroaromatic ring, which is unsubstituted or substituted with one or more substituents chosen from halo, hydroxyl, alkyl, haloalkyl, alkoxy, amino, mono- or dialkylamino, mono- or dihydroxyalkylamino and carboxyl radicals, or a ring of —O—$C_mH_{2m}$—O— type where m is an integer equal to 1 or 2. Preferably, A is unsubstituted or substituted with one or more groups chosen from a ($C_1$-$C_6$) alkylsulphonyl radical; a pyridinium or imidazolium group, which is unsubstituted or substituted with one or more substituents chosen from halo, hydroxyl, alkyl, haloalkyl, alkoxy, amino, mono- or dialkylamino, mono- or dihydroxyalkylamino and carboxyl radicals; a tri-($C_1$-$C_6$)alkylammonium group; a sulphonate radical. By way of example, A may be substituted with a methylsulphonyl radical; a 1-methylpyridinium group; an imidazolium group; a trimethylammonium group; a sulphonate radical.

According to one particular embodiment of the invention, X is chosen from a group $CR_1R_2$.

According to one particular embodiment of the invention, $R_1$ and $R_2$ are chosen from a $C_1$-$C_6$ alkyl radical. By way of example, $R_1$ and $R_2$ may be a methyl radical; an ethyl radical.

According to one particular embodiment of the invention, $R_3$ is chosen from a hydrogen atom.

According to one particular embodiment of the invention, W is chosen from a group $CR_4$.

According to one particular embodiment of the invention, $R_4$ is chosen from a hydrogen atom.

According to one particular embodiment of the invention, Y is chosen from an oxygen atom or a sulphur atom.

According to one particular embodiment of the invention, Z is chosen from a —$C_pH_{2p}$— group, with p being an integer between 2 and 4, which is unsubstituted or substituted with one or more substituents chosen from halo, hydroxyl, alkyl, haloalkyl, alkoxy, amino, mono- or dialkylamino, mono- or dihydroxyalkylamino and carboxyl radicals. By way of example, Z may be a —$C_2H_4$— group.

According to one particular embodiment of the invention, n is equal to 1 or 2.

According to one particular embodiment of the invention, B is a benzene, carbazole or indole nucleus.

According to one particular embodiment of the invention, B is unsubstituted or substituted with one or more groups that may be chosen from a halo radical, a $C_1$-$C_6$ alkyl radical, a $C_1$-$C_6$ alkoxy radical, a cyano radical, a trifluoromethyl radical, a $C_1$-$C_6$ alkyl-carbonyl radical, a trifluoromethylsulphonyl radical, a trifluoromethylcarbonyl radical, a phenylsulphonyl radical, a phenylcarbonyl radical, a phenyl radical which is unsubstituted or substituted with one or more substituents chosen from halo, hydroxyl, alkyl, haloalkyl, alkoxy, amino, mono- or dialkylamino, mono- or dihydroxyalkylamino and carboxyl radicals, an acylamino radical, a hydroxyl radical, an amino radical, a di(($C_1$-$C_6$)alkyl)amino radical, a hydroxy-($C_1$-$C_6$)alkylamino radical, a di(hydroxy ($C_1$-$C_6$)alkyl)amino radical, an (amino($C_1$-$C_6$)alkyl)amino radical, a di(amino($C_1$-$C_6$)alkyl)amino radical, a (($C_1$-$C_6$) alkyl)-(hydroxy($C_1$-$C_6$)alkyl)amino radical, an (amino ($C_1$-$C_6$)-alkyl) (($C_1$-$C_6$)alkyl)amino radical, an (amino($C_1$-$C_6$)-alkyl) (hydroxy($C_1$-$C_6$)alkyl)amino radical, a hydroxy-($C_1$-$C_6$)alkyl radical, an amino($C_1$-$C_6$)alkyl radical, a ($C_1$-$C_6$) alkylamino($C_1$-$C_6$)alkyl radical, a di(($C_1$-$C_6$)-alkyl)amino ($C_1$-$C_6$)alkyl radical, a (hydroxy($C_1$-$C_6$)-alkyl)amino($C_1$-$C_6$) alkyl radical, a di(hydroxy($C_1$-$C_6$)-alkyl)amino($C_1$-$C_6$)alkyl radical, an amino($C_1$-$C_6$)-alkylamino($C_1$-$C_6$)alkyl radical, a di(amino ($C_1$-$C_6$)-alkyl)amino($C_1$-$C_6$)alkyl radical, a (($C_1$-$C_6$)alkyl)(hydroxy($C_1$-$C_6$)alkyl)amino($C_1$-$C_6$)alkyl radical, a (($C_1$-$c_6$)alkyl)-(amino($C_1$-$C_6$)alkyl)amino radical, a (hydroxy($C_1$-$C_6$)-alkyl) (($C_1$-$C_6$)alkyl)amino($C_1$-$C_6$)alkyl radical, a phenyl($C_1$-$C_6$)alkyl radical which is unsubstituted or substituted with one or more substituents chosen from halo, hydroxyl, alkyl, haloalkyl, alkoxy, amino, mono- or dialkylamino, mono- or dihydroxyalkylamino and carboxyl radicals, a cationic group of the quaternary ammonium type, a ($C_1$-$C_6$)alkyl radical substituted with a cationic group of the quaternary ammonium type, a carboxyl radical, a ($C_1$-$C_6$) alkyl radical substituted with a carboxyl radical, a thiol radical, a thio($C_1$-$C_6$)alkyl radical, a sulphonate radical, a ($C_1$-$C_6$)alkyl radical substituted with a sulphonate radical, a ($C_1$-$C_6$)alkylcarbonyl ($C_1$-$C_6$) alkyl radical, a di(halo($C_1$-$C_6$)alkyl)amino radical, an acetamido radical, an aryloxy radical, an aryloxy($C_1$-$C_6$)alkyl radical, an ethenyl radical, an ethenylcarbonyl radical, a group $NR_6R_7$, $R_6$ and $R_7$ possibly forming, together with the nitrogen atom to which they are attached, a non-aromatic $C_5$, $C_6$ or $C_7$ ring, optionally interrupted with one or more heteroatoms such as a nitrogen, oxygen or sulphur atom, an alkylene chain possibly containing an oxygen or sulphur atom and possibly ending with a cyano, $C_1$-$C_6$ alkylsulphonyl or $C_1$-$C_6$ alkylcarbonyl group; two adjacent groups of B possibly forming an aromatic or heteroaromatic ring, which is unsubstituted or substituted with one or more substituents chosen from halo, hydroxyl, alkyl, haloalkyl, alkoxy, amino, mono- or dialkylamino, mono- or dihydroxyalkylamino and carboxyl radicals, or a ring of —O—$C_rH_{2r}$—O— type in which r represents an integer equal to 1 or 2. Preferably, B is unsubstituted or substituted with one or more groups chosen from a hydroxyl radical; an amino radical; a di(($C_1$-$C_6$)alkyl)amino radical; a $C_1$-$C_6$ alkyl radical; an acetamido radical; a pyridinium group; a tri($C_1$-$C_6$)alkylammonium group. By way of example, B may be substituted with a hydroxyl radical; an amino radical; a dimethylamino radical; an ethyl radical; an acetamido radical; a pyridinium group; a trimethylammonium group.

The cationic groups of the quaternary ammonium type may be chosen, for example, from trialkylammonium, oxazolium, thiazolium, imidazolium, pyrazolium, pyridinium, pyrrolium, triazolium, isoxazolium, isothiazolium, pyrimidinium, pyrazinium, triazinium, pyridazinium, indolium, quinolinium and isoquinolinium groups, which may be substituted or unsubstituted, and may be linked to the nucleus A or to the nucleus B via any of their unsubstituted carbon atoms.

Examples that may be mentioned of compounds of formula (I) for which Y is an oxygen atom include 9a-[2-[4-(dimethylamino)phenyl]-1,3-butadienyl]-2,3,9,9a-tetrahydro-9,9-dimethyloxazolo[3,2-a]indole-7-carboxylic acid; [9a-[2-[4-(dimethylamino)phenyl]ethenyl]-2,3,9,9a-tetrahydro-9,9-dimethyloxazolo[3,2-a]indol-7-yl]phosphonic acid; 4-[2-(9,9-diethyl-2,3-dihydro-7-methoxyoxazolo[3,2-a]indol-9a(9H)-yl)ethenyl]-N,N-diethylbenzenamine; [3-[9a-[2-[4-(dimethylamino)phenyl]ethenyl]-2,3,9,9a-tetrahydro-9,9-dimethyloxazolo[3,2-a]indol-7-yl]propyl]phosphonic acid; 4-[2-(2,3-dihydro-9,9-dimethyloxazolo[3,2-a]indol-9a(9H)-yl)ethenyl]-N-methyl-N-phenylbenzenamine; 4- [2-(2,3-dihydro-9,9-dimethyloxazolo[3,2-a]indol-9a(9H)-yl)ethenyl]-3-ethoxy-N,N-diethylbenzenamine; 4-[2-(2,3-dihydro-9,9-dimethyloxazolo[3,2-a]indol-9a(9H)-yl)-ethenyl]-N-ethyl-N-(2-methylpropyl)benzenamine; 4-[2-(2,3-dihydrooxazolo[3,2-a]indol-9a(9H)-yl)ethenyl]-N,N-dimethylbenzenamine; 4-[4-(2,3-dihydro-7,9,9-trimethyloxazolo[3,2-a]indol-9a(9H)-yl)-1,3-butadienyl]-N,N-dimethylbenzenamine; 4-[4-(2,3-dihydro-9,9-dimethyl-7-nitrooxazolo[3,2-a]indol-9a(9H)-yl)-1,3-butadienyl]-N,N-dimethylbenzenamine; 9a-[4-[4-(dimethylamino)phenyl]-1,3-butadienyl]-2,3,9,9a-tetrahydro-9,9-di-methyloxazolo[3, 2-a]indole-7-carbonitrile; 9a-[2-[4-(dimethylamino)phenyl ethenyl]-2,3,9,9a-tetrahydro-9,9-dimethyloxazolo[3,2-a] indole-7-carbonitrile; 4-[2-(2,3-dihydro-9,9-dimethyloxazolo[3,2-a]indol-9a(9H)-yl)-ethenyl]-N,N-dimethylbenzenamine; 9a-[2-[4-(dimethylamino)phenyl] ethenyl]-2,3,9,9a-tetrahydro-9,9-dimethyloxazolo[3,2-a] indole-7-sulphonic acid methyl ester; N,N-bis(2-chloroethyl)-4-[2-(2,3-dihydro-9,9-dimethyloxazolo[3,2-a]indol-9(9H)-yl)ethenyl]benzenamine; 9a-[2-[4-(dimethylamino)phenyl]ethenyl]-9,9a-di-hydro-9,9-dimethyl-7-(octylsulphonyl)oxazolo[3,2-a]-indol-2(3H)-one; 9a-[2-[4-(dimethylamino)phenyl]-ethenyl]-9,9a-dihydro-9,9-dimethyl-7-(phenylsulphonyl)-oxazolo[3,2-a]indol-2(3H)-one; 9a-[2-[4-(dimethylamino)phenyl]-1-methylethenyl]-9,9a-dihydro-9,9-dimethyl-7-(methylsulphonyl)oxazolo[3,2-a]indol-2(3H)-one; 9a-[2-[4-(dimethylamino)phenyl]ethenyl]-9,9a-dihydro-9,9-dimethyl-7-(methylsulphonyl)oxazolo[3,2-a]indol-2(3H)-one; 4-[2-[2,3-dihydro-9,9-dimethyl-7-(methylsulphonyl)oxazolo[3,2-a]indol-9a(9H)-yl]ethenyl]-N,N-dimethylbenzenamine; 4-[2-[9-(ethoxymethyl)-2,3-dihydro-9-methyl-7-(methylsulphonyl)oxazolo[3,2-a]indol-9a(9H)-yl]ethenyl]-N,N-dimethylbenzenamine; 4-[2-[2,3-dihydro-2,9,9-trimethyl-7-(methylsulphonyl)oxazolo-[3,2-a]indol-9a(9H)-yl]ethenyl]-N,N-dimethylbenzenamine; 4-[2-[2,3-dihydro-9,9-dimethyl-7-(methyl-sulphonyl)oxazolo[3,2-a]indol-9a(9H)-yl]-1-propenyl]-N,N-dimethylbenzenamine; N,N-dibutyl-4-[2-[2,3-dihydro-9,9-dimethyl-7-(methylsulphonyl)oxazolo[3,2-a]indol-9a(9H)-yl]ethenyl]benzenamine; 4-[2-[2,3-dihydro-9,9-dimethyl-7-(phenylsulphonyl)oxazolo[3,2-a]indol-9a(9H)-yl]ethenyl]-N,N-dimethyl; 4-[2-[2,3-dihydro-9,9-dimethyl-7-(octylsulphonyl)oxazolo[3,2-a]indol-9a(9H)-yl]ethenyl]-N,N-dimethylbenzenamine; N-[4-[2-[7-(butyl-sulphonyl)-2,3-dihydro-9,9-dimethyloxazolo[3,2-a]indol-9a(9H)-yl]ethenyl]phenyl] acetamide; 4-[2-[7-(butyl-sulphonyl)-2,3-dihydro-9,9-dimethyloxazolo[3,2-a]indol-9a(9H)-yl]ethenyl]-N,N-dimethylbenzenamine; 4-[4-[2,3-dihydro-9,9-dimethyl-7-(methylsulphonyl)oxazolo[3,2-a]-indol-9a(9H)-yl]-1,3-butadienyl]-N,N-dimethylbenzen-amine; 9a-[2-[4-(dimethylamino)phenyl]ethenyl]-2,3,9,9a-tetrahydro-9-methyloxazolo[3,2-a]indole-9-ethanol; 4-[2-(9,9-diethyl-2,3-dihydrooxazolo[3,2-a]-indol-9a(9H)-yl)ethenyl]-N,N-dimethylbenzenamine; 4-[2-[2,3-dihydro-9-methyl-9-(2-phenoxyethyl)oxazolo[3,2-a]-indol-9a(9H)-yl]ethenyl]-N,N-dimethylbenzenamine; 4-[2-[9-(ethoxymethyl)-2,3-dihydro-9-methyloxazolo[3,2-a]- indol-9a(9H)-yl]ethenyl]-N,N-dimethylbenzenamine; 4-[2-(11,11-dimethylbenz[e]oxazolo[3,2-a]indol-10a(11H)-yl)-ethenyl]-N,N-dimethylbenzenamine; 4-[2-(7-methoxy-9,9-dimethyloxazolo[3,2-a]indol-9a(9H)-yl)ethenyl]-N,N-dimethylbenzenamine; 4-[2-(9,9-dimethyloxazolo[3,2-a]-indol-9a(9H)-yl)ethenyl]-N,N-dimethylbenzenamine; 9a-[2-[4-(dimethylamino)phenyl]ethenyl]-3-ethyl-9,9a-dihydro-9,9-dimethyloxazolo[3,2-a]indol-2(3H)-one; 7-chloro-9a-[2-[4-(dimethylamino)phenyl]ethenyl]-9,9a-dihydro-3,9,9-trimethyloxazolo[3,2-a]indol-2(3H)-one; 9a-[2-[4-(dibutylamino)phenyl]ethenyl]-9,9a-dihydro-9,9-dimethyloxazolo[3,2-a]indol-2(3H)-one; 9a-[2-[4-(dimethylamino)phenyl]ethenyl]-9,9a-dihydro-9-(2-hydroxyethyl)-9-methyloxazolo[3,2-a]indol-2(3H)-one; 9a-[2-[4-(dimethylamino)phenyl]-1-propenyl]-9,9a-dihydro-9,9-dimethyloxazolo[3,2-a]indol-2(3H)-one; 9,9a-dihydro-7, 9,9-trimethyl-9a-[2-(4-nitrophenyl)-ethenyl]oxazolo[3,2-a] indol-2(3H)-one; N-[4-[2-(2,3-dihydro-9,9-dimethyl-2-oxooxazolo[3,2-a]indol-9a(9H)-yl)ethenyl]phenyl]acetamide; 9a-[2-[4-(dimethylamino)phenyl]ethenyl]-9,9a-dihydro-6-methoxy-9,9-dimethyl-oxazolo[3,2-a]indol-2 (3H)-one; 9a-[2-[4-(dimethylamino)phenyl]ethenyl]-2,3,9, 9a-tetrahydro-9,9-dimethyl-2-oxooxazolo[3,2-a]indole-7-carboxylic acid ethyl ester; 9a-[2-[4-(dimethylamino) phenyl]ethenyl]-9,9a-dihydro-7,9,9-trimethyloxazolo[3,2-a] indol-2(3H)-one; 10a-[2-[4-(dimethylamino)phenyl] ethenyl]-10a, 11-dihydro-11,11-dimethylbenz[e]oxazolo[3, 2-a]indol-9(8H)-one; 9,9a-dihydro-9,9-dimethyl-9a-[2-(4-nitrophenyl)-ethenyl]oxazolo[3,2-a]indol-2(3H)-one; 7-chloro-9a-[2-[4-(dimethylamino)phenyl]ethenyl]-9,9a-dihydro-9,9-dimethyloxazolo[3,2-a]indol-2(3H)-one; 9a-[2-[4-(dimethylamino)phenyl]ethenyl]-9,9a-dihydro-9,9-dimethyloxazolo[3,2-a]indol-2(3H)-one; 4-[2-(7-chloro-2,3-dihydro-9,9-dimethyloxazolo[3,2-a]indol-9a(9H)-yl) ethenyl]-N,N-dimethylbenzenamine; 4-[2-(2,3-dihydro-9,9-dimethyloxazolo[3,2-a]indol-9a(9H)-yl)ethenyl]-N,N-dimethylbenzenamine; 4-[2-(7-chloro-2,3-dihydro-2,9,9-trimethyloxazolo[3,2-a]indol-9a(9H)-yl)ethenyl]-N,N-dimethylbenzenamine; 4-[2-(2,3-dihydro-9,9-dimethyloxazolo[3,2-a]indol-9a(9H)-yl)-1-methylethenyl]-N,N-dimethylbenzenamine; 4-[2-(2,3-dihydro-9,9-dimethyloxazolo[3,2-a]indol-9a(9H)-yl)ethenyl]-N,N-diethylbenzenamine; 2,3,9,9a-tetrahydro-7-methoxy-9,9-dimethyl-9a-[2-(4-nitrophenyl)ethenyl]oxazolo[3,2-a]-indole; 4-[2-(2,3-dihydro-9,9-dimethyl-7-nitrooxazolo-[3,2-a]indol-9a(9H)-yl)ethenyl]-N,N-dimethylbenzenamine; N,N-dibutyl-4-[2-(2,3-dihydro-9,9-dimethyloxazolo[3,2-a]indol-9a(9H)-yl)ethenyl]benzenamine; 2,3,9,9a-tetrahydro-9,9-dimethyl-7-nitro-9a-[2-(4-nitrophenyl)ethenyl]oxazolo[3,2-a]indole; 7-chloro-2,3,9,9a-tetrahydro-9,9-dimethyl-9a-[2-(4-nitrophenyl)-ethenyl]oxazolo[3,2-a]indole; 4-[2-(2,3-dihydro-7-indol-9,9-dimethyloxazolo[3,2-a]indol-9a(9H)-yl)ethenyl]-N,N-dimethylbenzenamine; 4-[2-(2,3-dihydro-5-methoxy-9,9-dimethyloxazolo[3,2-a]indol-9a(9H)-yl) ethenyl]-N,N-dimethylbenzenamine; 4-[2-(2,3-dihydro-7-methoxy-9,9-dimethyloxazolo[3,2-a]indol-9a(9H)-yl) ethenyl]-N,N-dimethylbenzenamine; 4-[4-(2,3-dihydro-9,9-dimethyloxazolo[3,2-a]indol-9a(9H)-yl)-1,3-butadienyl]-N, N-diethylbenzenamine; 4-[4-(7-chloro-2,3-dihydro-9,9-dimethyloxazolo[3,2-a]indol-9a(9H)-yl)-1,3-butadienyl]-N, N-dimethylbenzenamine; 4-[4-(2,3-dihydro-9,9-dimethyloxazolo[3,2-a]indol-9a(9H)-yl)-1,3-butadienyl]-N, N-dimethylbenzenamine; 4-[4-(2,3-dihydro-7-methoxy-9,9-dimethyloxazolo[3,2-a]indol-9a(9H)-yl)-1,3-butadienyl]-N, N-dimethylbenzenamine; 2,3,9,9a-tetrahydro-7,9,9-trimethyl-9a-[2-(4-nitrophenyl)ethenyl]oxazolo-[3,2-a] indole; N-[4-[2-(2,3-dihydro-9,9-dimethyloxazolo[3,2-a] indol-9a(9H)-yl)ethenyl]phenyl]acetamide; 4-[2-(2,3-dihydro-6-methoxy-9,9-dimethyloxazolo[3,2-a]-indol-9a (9H)-yl)ethenyl]-N,N-dimethylbenzenamine; 4-[2-(8,9-dihydro-11,11-dimethylbenz[e]oxazolo[3,2-a]indol-10a (11H)-yl)ethenyl]-N,N-dimethylbenzenamine; 4-[2-(2,3-dihydro-7,9,9-trimethyloxazolo[3,2-a]indol-9a(9H)-yl) ethenyl]-N,N-dimethylbenzenamine; 2,3,9,9a-tetrahydro-9, 9-dimethyl-9a-[2-(4-nitrophenyl)ethenyl]-oxazolo[3,2-a] indole; 9,9a-dihydro-9,9-dimethyl-9a-[2-(9-methyl-9H-carbazol-3-yl)ethenyl]-7-(methylsulphonyl)oxazolo[3,2-a] indol-2(3H)-one; 9a-[2-(9-hexyl-9H-carbazol-3-yl)ethenyl]-2,3,9,9a-tetrahydro-9,9-dimethyl-7-(phenylsulphonyl) oxazolo[3,2-a]indole; 2,3,9,9a-tetrahydro-9,9-dimethyl-7-(methylsulphonyl)-9a-[2-(9-octyl-9H-carbazol-3-yl) ethenyl]oxazolo[3,2-a]-indole; 9a-[2-(9-butyl-6-methoxy-9H-carbazol-3-yl)-ethenyl]-2,3,9,9a-tetrahydro-9,9-dimethyloxazolo[3,2-a] indole-7-carboxylic acid ethyl ester; 9a- [2- (9-ethyl-9H-carbazol-3-yl)ethenyl]-2,3,9,9a-tetrahydro-9,9-dimethyloxazolo[3,2-a]indole-7-sulphonic acid methyl ester; 3-chloro-6-[2-[2,3-dihydro-9,9-dimethyl-7-(methylsulphonyl)oxazolo[3,2-a]indol-9a(9H)-yl]ethenyl]-9-octyl-9H-carbazole; 3-[2-[2,3-dihydro-9,9-dimethyl-7-(methylsulphonyl)oxazolo[3,2-a]indol-9a(9H)-yl]ethenyl]-9-methyl-9H-carbazole; 3-[2-[9-(2-ethoxyethyl)-2,3-dihydro-9-methyl-7-(methylsulphonyl)oxazolo[3,2-a]indol-9a(9H)-yl]ethenyl]-9H-carbazole; 9a-[2-(9-hexyl-9H-carbazol-3-yl)ethenyl]-2,3,9,9a-tetrahydro-9-(2-hydroxyethyl)-9-methyloxazolo[3,2-a]indole-7-carboxylic acid ethyl ester; 2,3,9,9a-tetrahydro-9,9-dimethyl-9a-[2-(9-octyl-9H-carbazol-3-yl)ethenyl]oxazolo[3,2-a]indole-7-carboxylic acid ethyl ester; 9a-[2-(9-butyl-9H-carbazol-3-yl) ethenyl]-2,3,9,9a-tetrahydro-9,9-dimethyloxazolo[3,2-a] indole-7-carboxylic acid ethyl ester; 2,3,9,9a-tetrahydro-9,9-dimethyl-9a-[2-(9-methyl-9H-carbazol-3-yl)ethenyl] oxazolo[3,2-a]indole-7-carboxylic acid ethyl ester; 9a-[2-(9-butyl-6-ethoxy-9H-carbazol-3-yl)ethenyl]-2,3,9,9a-tetrahydro-N,N,9,9-tetramethyloxazolo[3,2-a]indol-7-amine; 2,3,9,9a-tetrahydro-9-methyl-9a-[2-(9-methyl-9H-carbazol-3-yl)-ethenyl]oxazolo[3,2-a]indole-9-ethanol; 9a-[2-(9-butyl-9H-carbazol-3-yl)ethenyl]-2,3,9,9a-tetrahydro-N,N,9,9-tetramethyloxazolo[3,2-a]indol-7-amine; 3-[2-(2,3-dihydro-6-methoxy-9,9-dimethyloxazolo[3,2-a]indol-9a (9H)-yl)ethenyl]-9-methyl-9H-carbazole; 3-[2-(2,3-dihydro-9,9-dimethyloxazolo[3,2-a]indol-9a(9H)-yl)-1-propenyl]-9-methyl-9H-carbazole; 3-[2-(7-chloro-2,3-dihydro-9,9-dimethyloxazolo[3,2-a]indol-9a(9H)-yl)-ethenyl]-9-methyl-9H-carbazole; 3-bromo-6-[2-(2,3-dihydro-9,9-dimethyloxazolo[3,2-a]indol-9a(9H)-yl]-ethenyl]-9-ethyl-9H-carbazole; 3-[2-[2,3-dihydro-9,9-dimethyloxazolo[3,2-a]indol-9a(9H)-yl)ethenyl]-9-methyl-9H-carbazole.

Preferably, the compound(s) of formula (I) for which Y represents an oxygen atom is (are) chosen from the compounds given in the table below:

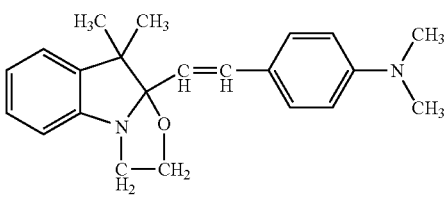

Dye 1

-continued
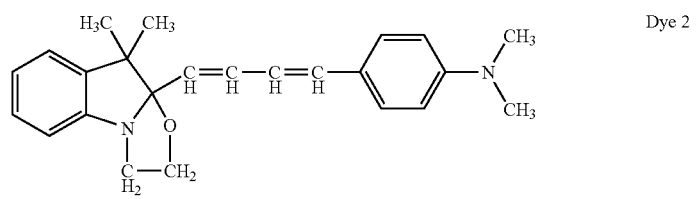
Dye 2
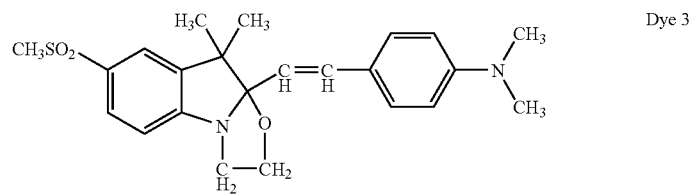
Dye 3
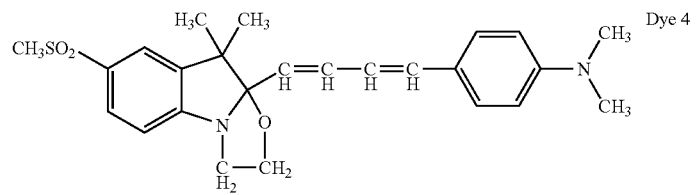
Dye 4
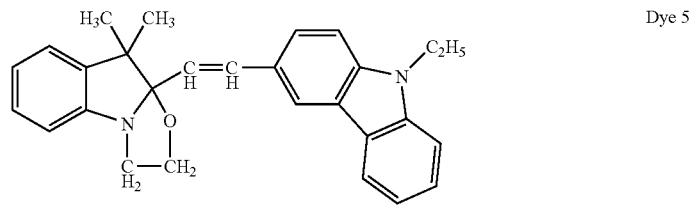
Dye 5
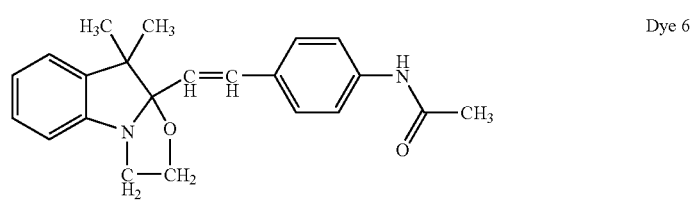
Dye 6
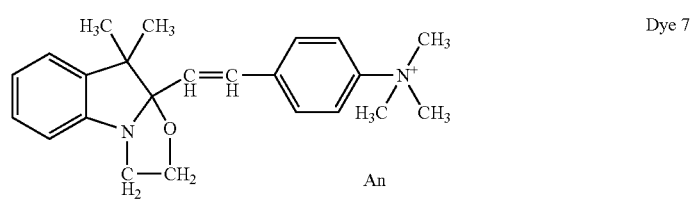
Dye 7
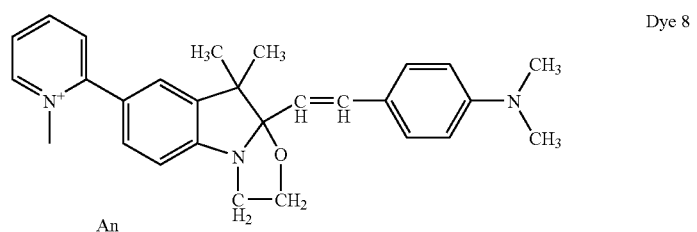
Dye 8

-continued

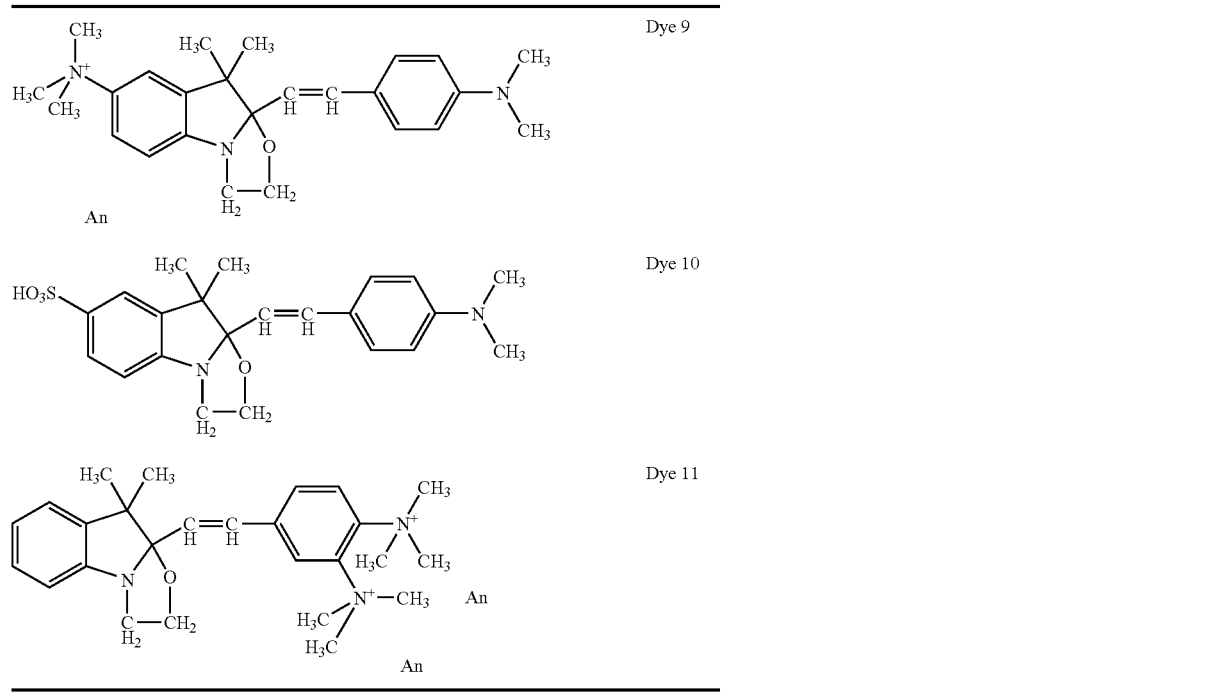

In the above table, An represents a counterion as defined above.

Preferably, the compounds are chosen from dyes 1 to 6 and 8 above.

As examples of compounds of formula (I) for which Y is a sulphur atom, mention may be made of 3,3-dimethyl-2-(p-dimethylaminostyryl)indolino[1,2-b]thiazoline; 3,3,5-trimethyl-2-(p-dimethylaminostyryl)indolino[1,2-b]thiazoline; 3,3,5-trimethyl-2-(p-chlorostyryl)indolino[1,2-b]thiazoline; 3,3,5-trimethyl-2-[2-(thienyl)-vinyl]indolino[1,2-b]thiazoline; 3,3-dimethyl-5-methoxy-2-[2-(9-ethylcarbazolyl)vinyl]indolino[1,2-b]-thiazoline; 3,3-dimethyl-5-carboethoxy-2-(p-dimethylaminostyryl)indolino[1,2-b]thiazoline; 3,3-dimethyl-5-chloro-2-[2-(benzothiazolyl)vinyl]indolino[1,2-b]-thiazoline; 3,3-dimethyl-5-methoxy-2-(p-dimethylamino-styryl)indolino[1,2-b]thiazoline; 3,3-dimethyl-5-carbo-ethoxy-2-(3,4-methylenedioxystyryl)indolino[1,2-b]-thiazoline; 3,3-dimethyl-5-chloro-2-(p-methylstyryl)-indolino[1,2-b]thiazoline; 3,3-dimethyl-5-chloro-2-(p-methoxystyryl]indolino[1,2-b]thiazoline; 3,3,5-trimethyl-2-(p-acetylaminostyryl)indolino[1,2-b]-thiazoline; 3,3-dimethyl-5-methoxy-2-(3-hydroxy-4-methoxystyryl)indolino[1,2-b]thiazoline; 3,3-dimethyl-5-carboethoxy-2-(o-cyanostyryl)indolino[1,2-b]thiazoline; 3,3-dimethyl-5-chloro-2-(p-dimethylaminostyryl)-indolino [1,2-b]thiazoline; 3,3-dimethyl-5-methyl-sulphonyl-2-(p-dimethylaminostyryl)indolino[1,2-b]thiazoline; 3,3-dimethyl-5-phenylsulphonyl-2-(p-dimethylaminostyryl) indolino[1,2-b]thiazoline; 3,3-dimethyl-5-ethoxycarboxy-2-(p-dimethylaminostyryl)indolino[1,2-b]-oxazoline.

The compounds of formula (I) present in the dye composition used in the context of the invention may be prepared, for example, according to the preparation modes as described in patents FR 2 285 439 and U.S. Pat. No. 4,380,629. These preparation modes may be adapted to the cationic compounds of formula (I) by adding a quaternization step.

By way of example of synthesis of a compound of formula (I) with Y representing an oxygen atom, the synthesis of dye 8 may be performed according to the following reaction scheme:

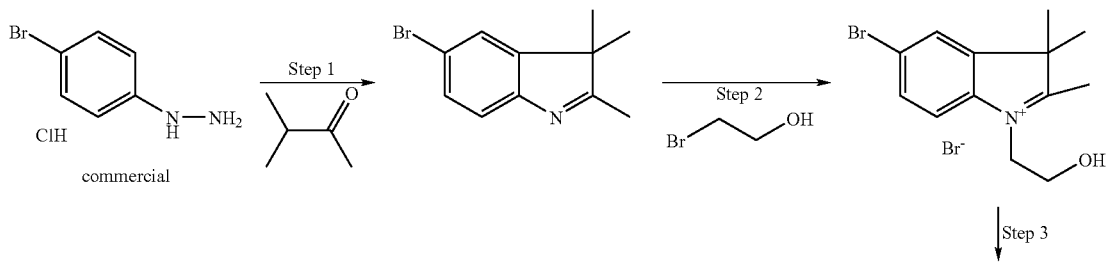

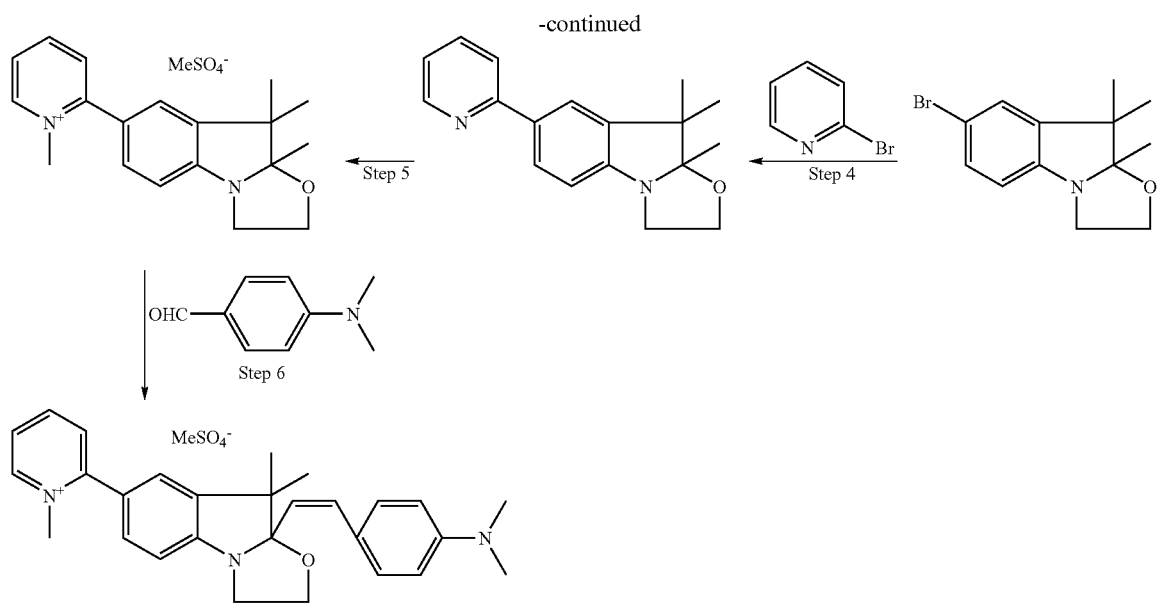

As an example of synthesis of a compound of formula (I) with Y representing a sulphur atom, it is possible to perform the synthesis as follows:

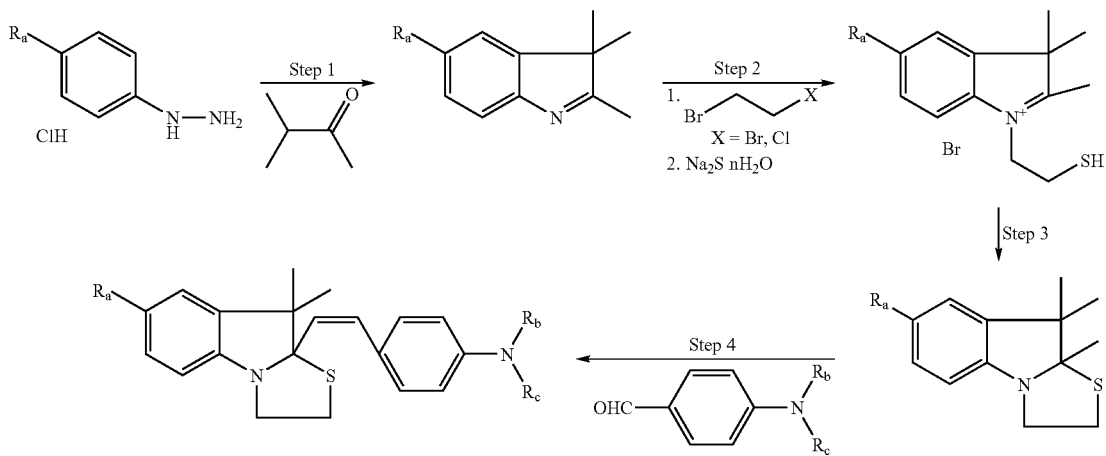

The compound(s) chosen from the compounds of formula (I), and the addition salts thereof, generally represent(s) from 0.0001% to 30% by weight relative to the total weight of the dye composition, more particularly from 0.001% to 10% by weight relative to the total weight of the dye composition and preferably from 0.01% to 5% by weight relative to the total weight of the dye composition.

In general, the addition salts of the compounds of formula (I) that may be used in the context of the invention are especially chosen from the acid-addition salts such as the hydrochlorides, hydrobromides, sulphates, methosulphates, gluconates, citrates, succinates, tartrates, lactates, tosylates, benzenesulphonates, phosphates and acetates, and the salts of addition with a base such as sodium hydroxide, potassium hydroxide, ammonia and amines, including alkanolamines.

According to one advantageous variant of the present invention, the dye composition used in the process comprises at least one thiol compound other than the compounds of formula (I), comprising at least one thiol function (SH) and a saturated or unsaturated group containing from 1 to 20 carbon atoms, said group being optionally interrupted with one or more nonadjacent groups (separated by at least one carbon atom) chosen from —O—, —S—, —S—S—, amino (—NR—), carbonyl (—CO—), oxycarbonyl (—O—CO—), aminocarbonyl (—NR—CO—), aromatic or heteroaromatic nucleus, the amino groups being unsubstituted or substituted with one or two $C_1$-$C_6$ alkyl radicals; on condition that the sulphur atom of the thiol function is attached to said group via a carbon atom.

Moreover, the group containing from 1 to 20 carbon atoms may be optionally substituted with one or more hydroxyl, $C_1$-$C_6$ alkoxy, hydroxycarbonyl, ($C_1$-$C_6$)alkoxycarbonyl, amino, aminocarbonyl or alkylcarbonylamino, in which the amino function is unsubstituted or substituted with one or two $C_1$-$C_6$ alkyl radicals.

Preferably, the thiol compound comprises one or two thiol functions (SH), preferably a thiol function, and a saturated group containing from 2 to 10 carbon atoms, said group being optionally interrupted with a group chosen from carbonyl (—CO—) and oxycarbonyl (—O—CO—) groups; on condition that the sulphur atom of the thiol function is attached to said group via a carbon atom.

Moreover, the group may be optionally substituted with one or more hydroxyl, ($C_1$-$C_6$)alkoxycarbonyl, or amino that is unsubstituted or substituted with one or two $C_1$-$C_6$ alkyl radicals.

In accordance with one particular embodiment of the invention, the thiol compound is chosen from thioglycolic acid, thiolactic acid, mercaptopropionic acid, cysteamine, thiosuccinic acid, cysteine, acetylcysteine, glyceryl thioglycolate, thioglycerol, alkali metal (sodium or potassium), alkaline-earth metal (calcium) or ammonium salts thereof, and also mixtures thereof.

Usually, the content of thiol compound is between 0.001% and 30% by weight relative to the total weight of the dye composition, more particularly between 0.01% and 15% by weight relative to the total weight of the dye composition, preferably between 0.1% and 10% by weight relative to the total weight of the dye composition and even more preferably between 0.5% and 5% by weight relative to the total weight of the dye composition.

It should be noted that the thiol compound may be mixed with the composition comprising the compound(s) of formula (I) and thus stored. According to another possibility, the thiol compound is mixed with the composition comprising the compound(s) of formula (I) only at the time of use of said composition.

The dye composition used in the context of the present invention may also comprise one or more additional direct dyes, which may be chosen especially from nitrobenzene dyes, azo direct dyes, methine direct dyes and natural dyes. These direct dyes may be of nonionic, anionic or cationic nature.

When they are present, the content of additional direct dye(s) generally represents from 0.001% to 20% by weight relative to the total weight of the dye composition and preferably from 0.01% to 10% by weight relative to the total weight of the dye composition.

The composition according to the invention may also comprise one or more oxidation dyes chosen from the oxidation bases and couplers conventionally used in oxidation dyeing.

The oxidation bases may be chosen from para-phenylenediamines, bis(phenyl)alkylenediamines, para-aminophenols, bis-para-aminophenols, ortho-amino-phenols, ortho-phenylenediamines and heterocyclic bases, and the addition salts thereof.

The couplers may be chosen from meta-phenylenediamines, meta-aminophenols, meta-diphenols, naphthalene-based couplers and heterocyclic couplers, and the addition salts thereof.

When they are present, the content of oxidation dye(s) generally represents from 0.001% to 20% by weight relative to the total weight of the dye composition and preferably from 0.01% to 10% by weight relative to the total weight of the dye composition.

In accordance with one preferred embodiment of the invention, the dye composition does not comprise any additional direct dye or any oxidation dye.

The dye composition used in the process according to the invention may also comprise one or more acidifying agents other than the compounds of formula (II) and/or one or more basifying agents usually used in the dyeing of keratin fibres.

Among the acidifying agents that may be mentioned, for example, are mineral acids, for instance hydrochloric acid, nitric acid or sulphuric acid, or organic acids, for instance compounds comprising at least one carboxylic acid function, such as acetic acid, tartaric acid, citric acid, lactic acid, succinic acid or malic acid, a sulphonic acid function, a phosphonic acid function or a phosphoric acid function.

Among the basifying agents that may be mentioned, for example, are:

basic amino acids;

alkali metal or alkaline-earth metal carbonates or bicarbonates;

silicates or metasilicates;

the compounds of formula (III) below:

$$X(OH)_n \qquad (III)$$

in which:

X represents a potassium, lithium, sodium or ammonium ion $N^+R_8R_9R_{10}R_{11}$ with $R_8$, $R_9$, $R_{10}$ and $R_{11}$, which may be identical or different, denoting a $C_2$-$C_4$ alkyl radical when n is equal to 1;

X represents a magnesium or calcium atom when n is equal to 2;

and in particular sodium or potassium hydroxide;

the compounds of formula (IV) below:

(IV)

in which:

$R_{12}$ represents a hydrogen atom; a $C_1$-$C_6$ alkyl radical; a $C_1$-$C_6$ monohydroxyalkyl radical; a $C_2$-$C_6$ polyhydroxyalkyl radical;

$R_{13}$ and $R_{14}$, which may be identical or different, represent a hydrogen atom; a $C_1$-$C_6$ alkyl radical; a $C_1$-$C_6$ monohydroxyalkyl radical; a $C_2$-$C_6$ polyhydroxyalkyl radical;

and in particular ammonia and alkanolamines such as monoethanolamine, diethanolamine and triethanolamine, and derivatives thereof;

the compounds of formula (V) below:

(V)

in which:

W is a propylene residue optionally substituted with a hydroxyl group or a $C_1$-$C_4$ alkyl radical;

$R_{15}$, $R_{16}$, $R_{17}$ and $R_{18}$, which may be identical or different, represent a hydrogen atom or a $C_1$-$C_4$ alkyl or $C_1$-$C_4$ hydroxyalkyl radical.

For the purposes of the present invention, the term "basic amino acid" means either (i) an amino acid containing, in addition to the amine function located α to the carboxyl group, an additional cationic (or basic) group; or (ii) an amino acid containing a cationic (or basic) side chain (hydrophilic); or (iii) an amino acid bearing a side chain consisting of a nitrogenous base. These definitions are generally known and published in general biochemistry texts such as J. H. Weil (1983) pages 5 et seq., Lubert Stryer (1995) page 22, A. Lehninger (1993) pages 115-116 and de Boeck-Wesmael (1994) pages 57-59.

The basic amino acids in accordance with the invention are preferably chosen from those corresponding to formula (D) below:.

in which $R_{19}$ denotes a group chosen from:

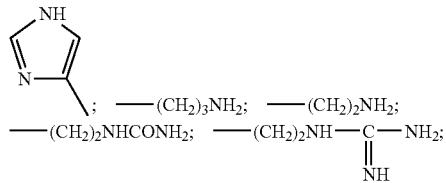

Among the compounds of formula (D) that may be mentioned, for example, are histidine, lysine, ornithine, citrulline and arginine.

The suitable dyeing medium, also known as the dye support, generally consists of water or of at least one organic solvent, or of a mixture of water and of at least one organic solvent. Examples of organic solvents that may be mentioned include ketones such as acetone; linear or branched monoalcohols or diols, which are preferably saturated, containing 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; polyols or polyol ethers, for instance ethylene glycol monomethyl, monoethyl and monobutyl ethers, 2-butoxyethanol, propylene glycol or ethers thereof, for instance propylene glycol monomethyl ether, butylene glycol or dipropylene glycol; and also diethylene glycol alkyl ethers, especially of $C_1$-$C_4$, for instance diethylene glycol monoethyl ether or monobutyl ether, alone or as a mixture.

The solvents are generally present in proportions of between 1% and 40% by weight relative to the total weight of the dye composition, and preferably between 5% and 30% by weight relative to the total weight of the dye composition.

The dye composition may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric associative polymeric thickeners, antioxidants, penetrants, sequestrants, fragrances, buffers, dispersants, conditioning agents, for instance cationic or amphoteric polymers, cations, volatile or nonvolatile, modified or non-modified silicones, chitosans or chitosan derivatives, film-forming agents, ceramides, preserving agents and opacifiers.

The above adjuvants are generally present in an amount for each of between 0.01% and 20% by weight relative to the total weight of the dye composition.

Needless to say, a person skilled in the art will take care to select this or these optional additional compounds such that the advantageous properties intrinsically associated with the dye composition that is useful in the context of the invention are not, or are not substantially, adversely affected by the envisaged addition(s).

According to one variant of the invention, the pH of the dye composition is greater than the pKa of the compound of formula (I) and less than or equal to 12. Advantageously, the pH is between 8 and 12. In the context of this variant, the compound is in a substantially colourless form.

The dye composition may be in various forms, such as in the form of liquids, creams or gels, or in any other form that is suitable for dyeing keratin fibres, and especially human hair.

As has been stated previously, the dyeing process in accordance with the invention is a process in which the dye composition that has just been described is applied to wet or dry keratin fibres, in combination with a revealing composition comprising at least one compound of formula (II) or a precursor thereof.

Preferably, the compound of formula (II) or the precursor thereof is chosen and used such that it is soluble at 25° C. in the medium of the revealing composition. If the medium is a one-phase medium, the compound of formula (II) or the precursor thereof is soluble in this phase; if it is a multiphase medium, the compound of formula (II) or the precursor thereof is soluble in at least one of these phases.

The medium of this revealing composition may be an aqueous or nonaqueous medium. Thus, it may be constituted at least by water or by at least one organic solvent that is at least partially water-soluble, or alternatively by a mixture of water and of at least one organic solvent that is at least partially water-soluble, the assembly forming one or more phases. For further details, reference may be made to the account given previously in the context of the description of the medium of the dye composition. The medium of the revealing composition may also comprise a water-insoluble solvent, for instance plant or mineral oils, volatile or nonvolatile silicones, or a mixture of water and of such solvents, in emulsified or non-emulsified form.

As indicated previously, the compound used in the revealing composition is a compound of formula (II) $R_6(R_7CR_8)_n$—COOX, or a precursor of such a compound.

In this formula:

$R_6$ represents a fused or non-fused, 5- to 16-membered nucleus of aromatic or heteroaromatic type comprising at least one nitrogen, oxygen or sulphur atom, optionally substituted with one or more hydroxyl, $C_1$-$C_3$ alkoxy, hydroxycarbonyl, alkoxycarbonyl with the alkoxy group being $C_1$-$C_3$, amino or cyano groups;

n is an integer ranging from 0 to 6;

$R_7$ and $R_8$ represent, independently of each other, a hydrogen atom, a linear or branched, substituted or unsubstituted $C_1$-$C_6$ alkyl group, a hydroxyl group, a $C_1$-$C_6$ methoxy group, a cyano group, an amino group or a hydroxycarbonyl or alkoxycarbonyl group;

X represents a hydrogen atom, a monovalent cation more particularly such as a cation of an alkali metal such as sodium or potassium, or an ammonium cation.

It is moreover recalled that the precursors of the compounds of formula (II) are compounds capable of releasing into the medium of the revealing composition, and under the conditions for the use of this composition, a compound of formula (II). More particularly, esters of the acids corresponding to formula (II) that are capable of releasing the acid under acidic pH conditions are denoted. By way of example, tannic acid is a precursor of gallic acid.

In the compound of formula (II), the aromatic or heteroaromatic nucleus is more particularly chosen from nuclei of furan, pyrrole, pyrazole, imidazole, oxazole, thiazole, oxadiazole, triazole, triazole, thiadiazole, benzene, pyridine, pyridazine, pyrimidine, pyrazine, triazine, naphthalene, anthracene, quinoline or indole type; these nuclei being optionally substituted with one or more hydroxyl, $C_1$-$C_3$ alkoxy, hydroxycarbonyl, alkoxycarbonyl with the alkoxy group being $C_1$-$C_3$, amino or cyano groups, and preferably hydroxyl.

Preferably, the aromatic or heteroaromatic nucleus of formula (II) is chosen from benzene, pyridine, quinoline, triazine and indole nuclei; these nuclei optionally being substituted with one or more hydroxyl, $C_1$-$C_3$ alkoxy, hydroxycarbonyl, alkoxycarbonyl with the alkoxy group being $C_1$-$C_3$, amino or cyano groups, and preferably hydroxyl.

More particularly, the composition according to the invention does not comprise benzoic acid as sole compound of formula (II).

According to one particularly advantageous embodiment, the aromatic or heteroaromatic nucleus of formula (II) is chosen from benzene optionally substituted with one or more hydroxyl groups.

Preferably, the compound of formula (II) is chosen from gallic acid, 3,5-dihydroxybenzoic acid, p-hydroxybenzoic acid, 2,4-dihydroxybenzoic acid, 3,4-dihydroxybenzoic acid, 2,3-dihydroxybenzoic acid, 2,5-dihydroxybenzoic acid and 2,5-dihydroxyphenylacetic acid, salts thereof or precursors thereof, and preferably from 3,5-dihydroxybenzoic acid or salts or precursors thereof.

The content of compound of formula (II) or precursor thereof is usually between 0.001% and 50% by weight relative to the total weight of the dye composition, preferably between 0.1% and 30% by weight relative to the total weight of the dye composition and more advantageously between 0.1% and 15% by weight relative to the total weight of the dye composition.

The revealing composition may also comprise other adjuvants such as those listed in the context of the description of the dye composition, preferably with the exception of dyeing substances. Reference may thus be made to the details given previously regarding this subject.

According to a first embodiment of the invention, the revealing composition is applied simultaneously with the dye composition. In other words, the dye composition and the revealing composition are mixed together before applying the assembly to the keratin fibres.

According to a second embodiment of the invention, the revealing composition is applied before the dye composition.

According to this embodiment, it is preferable, before applying the dye composition, to rinse the keratin fibres with water in order to remove the excess of compound of formula (II).

According to a third embodiment of the invention, the revealing composition is applied after the dye composition.

According to this embodiment, it is not necessary to rinse the keratin fibres with water before applying the revealing composition, even though it may be envisioned to do so.

Whatever the embodiment used, it is possible to apply the revealing composition in combination with at least one additional revealing agent such as light, an electrical current, heat, an acidifying agent other than the compounds of formula (II), a solvent, an electromagnetic radiation or a combination of several of these agents.

If a post-treatment with at least one additional revealing agent is envisioned, this step may be performed with any of the abovementioned agents.

If a pretreatment with at least one additional revealing agent is envisioned, this step may be advantageously performed with an acidifying agent, a solvent or a combination thereof.

In this case also, it is preferable to perform rinsing with water before applying the dye composition.

When the coloration is revealed by the action of heat, the keratin fibres may be heated using a hood, a hairdryer, a crimping iron or a smoothing iron.

As regards the nature of the acidifying agents and solvents, reference may be made to the account given previously in the description.

However, advantageously, when the additional revealing agent is an acidifying agent, it is preferred to use at least one organic acid, for instance compounds comprising at least one carboxylic acid function such as acetic acid, tartaric acid, citric acid, lactic acid, succinic acid or malic acid.

The interval between a pretreatment step and the application of the dye composition, or alternatively between the application of the dye composition and a post-treatment step, may be between 5 minutes and 1 hour.

It is similarly possible, in certain cases, to reduce this interval to zero, which amounts to applying the dye composition immediately after applying the revealing composition in the case of a pretreatment step, or alternatively to performing the post-treatment step immediately after applying the dye composition in the case of a post-treatment step.

In accordance with another particular embodiment of the invention, although not a preferred embodiment, the dye composition according to the invention is applied in the presence of an oxidizing agent.

According to a first possibility, the oxidizing agent and the composition comprising the compound(s) of formula (I) are applied simultaneously. In this case, simultaneous dyeing and bleaching of the keratin fibres is performed. According to this possibility, the oxidizing agent is preferably added to the dye composition just at the time of use.

According to a second possibility, the oxidizing agent is applied once the composition comprising the compound(s) of formula (I) has (have) been applied.

The oxidizing agent may be chosen from hydrogen peroxide, urea peroxide, alkali metal bromates, persalts, peracids and enzymes of oxidase type.

The leave-on time for the dye composition optionally comprising an oxidizing agent, or the application or leave-on time for the revealing composition or for the revealing agent or the application time for the composition comprising an oxidizing agent, is generally between 5 minutes and 1 hour and preferably between 15 minutes and 1 hour.

The application temperature of the dye composition, of the revealing composition or of the revealing agent or of the oxidizing composition is generally set between room temperature and 80° C. and preferably between room temperature and 60° C. It should be noted that when the revealing agent is heat, the application temperature is between 60 and 120° C.

A subject of the present invention is also a multicompartment device for performing the process for dyeing keratin fibres in accordance with the invention.

The multicompartment device of the invention contains in a first compartment a composition comprising at least one compound chosen from the compounds of formula (I), and the addition salts thereof, and in a second compartment at least one compound of formula (II), or a precursor thereof, defined previously.

According to one particular embodiment, when a thiol compound is present, this thiol may be either in a third compartment, or mixed with the compound(s) of formula (I) in the first compartment.

According to another particular embodiment of the invention, the multicompartment device of the invention contains in an additional compartment at least one oxidizing agent as defined previously.

Finally, the invention also relates to a process for effacing the coloration obtained using the composition according to the invention.

It should be noted that this process is particularly suitable when the dye composition giving rise to the coloration does not comprise either any oxidation dye precursor (oxidation base or coupler) or any additional direct dye other than the compounds of formula (I).

With this aim, the dyed keratin fibres in accordance with the invention are treated with an effacing composition comprising at least one basifying agent as described previously, in a content such that the pH of the treated fibres is greater than the pKa of the compound(s) of formula (I) present in the composition giving rise to the coloration.

The composition for effacing the coloration may also contain one or more solvents, and various adjuvants conventionally used in the field and such as those described above.

The effacing composition is applied to the wet or dry fibres, usually with a leave-on time of between 5 minutes and 1 hour and preferably between 5 and 30 minutes.

Conventionally, the application temperature of this composition is between room temperature and 80° C. and preferably between room temperature and 60° C.

The examples that follow serve to illustrate the invention without, however, being limiting in nature.

EXAMPLE 1

The formulation below is prepared:

|  | weight % |
|---|---|
| Dye (*) | 0.07% |
| Benzyl alcohol | 5% |
| Ethanol | 25.2% |
| Monoethanolamine | 2% |
| Ammonium thioglycolate (71% AM) | 3.34% |
| Hydroxyethylcellulose (MW 720 000) | 1.5% |
| Distilled water | qs 100% |

(*) dye:

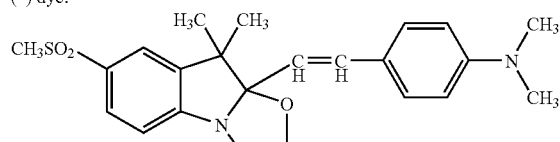

The formulation is applied to locks of natural hair containing 90% white hairs, with a leave-on time of 30 minutes at room temperature.

After dyeing, the hair is rinsed with clean water and then drained dry and post-treated as follows in order to reveal the colour:

|  | A | B |
|---|---|---|
| Gallic acid monohydrate | 9.4% | — |
| 3,5-Dihydroxybenzoic acid | — | 7.7% |
| Aqueous NaOH | qs pH 3.0 | qs pH 3.0 |
| Distilled water | qs 100 g | qs 100 g |

Each post-treatment is applied in leave-in manner at room temperature.

After the post-treatment, the hair is drained dry and dried at 60° C.

Once the locks are dry, the colour of each lock is measured using a CM3600d calorimeter in the L*a*b* system (specular components included, illuminant D65, angle 10°).

It is recalled that the lower the coefficient L*, the stronger the coloration obtained.

|  | L* |
|---|---|
| Uncoloured hair | 63.8 |
| Post-treatment A | 39.2 |
| Post-treatment B | 31.1 |

It is found that the intensity of the coloration obtained is considerably higher than that of the uncolored hair.

EXAMPLE 2

The process is performed as in Example 1, except that the following post-treatments are performed:

|  | C | D | E | F | G |
|---|---|---|---|---|---|
| p-Hydroxybenzoic acid | 6.9% | — | — | — | — |
| 2,4-Dihydroxybenzoic acid | — | 7.7% | — | — | — |
| 3,4-Dihydroxybenzoic acid | — | — | 7.7% | — | — |
| 2,3-Dihydroxybenzoic acid | — | — | — | 7.7% | — |
| 2,5-Dihydroxybenzoic acid | — | — | — | — | 7.7% |
| Ethanol | 50% | 50% | 50% | 50% | 50% |
| Aqueous NaOH | qs pH 3.0 | qs pH 3.0 | qs pH 3.0 | qs pH 3.0 | qs pH 3.0 |
| Distilled water | qs 100 g | qs 100 g | qs 100 g | qs 100 g | qs 100 g |

The calorimetric results are collated below:

|  | L* |
|---|---|
| Uncoloured hair | 63.8 |
| Post-treatment C | 42.1 |
| Post-treatment D | 35.3 |
| Post-treatment E | 35.3 |
| Post-treatment F | 38.1 |
| Post-treatment G | 35.5 |

EXAMPLE 3

The process is performed as in Example 1, except that the following post-treatment is performed to reveal the coloration:

|  | H (weight %) |
| --- | --- |
| Tannic acid | 16.1% |
| Aqueous HCl | qs pH 3.0 |
| Distilled water | 100 g |

This post-treatment is applied in leave-in manner at room temperature.

After the post-treatment, the hair is drained dry and dried at 60° C.

The colorimetric results are collated below:

|  | L* |
| --- | --- |
| Uncoloured hair | 63.8 |
| Post-treatment H | 43.3 |

The invention claimed is:

1. Process for dyeing keratin fibres, consisting in bringing said fibres into contact with a dye composition comprising, in a suitable dyeing medium, at least one compound of formula (I), and the addition salts thereof:

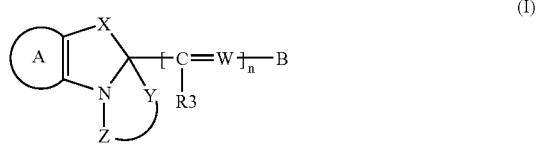

(I)

in which:

A is a substituted or unsubstituted, 5- to 16-membered, fused or non-fused aromatic or heteroaromatic nucleus;

X represents an oxygen atom, a sulphur atom or a group $CR_1R_2$;

$R_1$ and $R_2$ represent, independently of each other, a hydrogen atom, a $C_1$-$C_6$ alkyl radical, a $C_1$-$C_6$ hydroxyalkyl radical, a $C_1$-$C_6$ alkoxyalkyl radical or an alkylene chain that may contain an oxygen or sulphur atom; $R_1$ and $R_2$ may together form an aromatic or non-aromatic 5- or 6-membered ring optionally containing one or more heteroatoms such as a nitrogen, oxygen or sulphur atom;

$R_3$ represents a hydrogen atom, a halogen atom, a $C_1$-$C_6$ alkyl radical, a cyano radical, an aromatic group, a phenoxy group or a nitro radical;

W represents a group $CR_4$ or a nitrogen atom;

$R_4$ represents a hydrogen atom, a halogen atom, a $C_1$-$C_6$ alkyl radical, a cyano radical, an aromatic group, a phenoxy radical or a nitro radical;

Y represents an oxygen atom, a sulphur atom or a group $NR_5$;

$R_5$ represents a hydrogen atom or a $C_1$-$C_6$ alkyl radical;

Z represents a group —$C_pH_{2p}$—, with p being an integer between 2 and 4, which may be unsubstituted or substituted with one or more substituents chosen from halo, hydroxyl, alkyl, haloalkyl, alkoxy, amino, mono- or dialkylamino, mono- or dihydroxyalkylamino and carboxyl radicals; a group —$C_qH_{2q}CO$—, with q being an integer between 1 and 3, which may be unsubstituted or substituted with one or more substituents chosen from halo, hydroxyl, alkyl, haloalkyl, alkoxy, amino, mono- or dialkylamino, mono- or dihydroxyalkylamino and carboxyl radicals;

n represents an integer from 1 to 4;

B represents a substituted or unsubstituted, 5- to 16-membered, fused or non-fused aromatic or heteroaromatic nucleus, and b) at least one compound of formula (II) $R_6(R_7CR_8)_n$—COOX, or a precursor of such a compound, in which formula:

$R_6$ represents a fused or non-fused, 5- to 16-membered nucleus of aromatic or heteroaromatic type comprising at least one nitrogen, oxygen or sulphur atom, optionally substituted with one or more hydroxyl, $C_1$-$C_3$ alkoxy, hydroxycarbonyl, alkoxycarbonyl with the alkoxy group being $C_1$-$C_3$, amino or cyano groups;

n is an integer ranging from 0 to 6;

$R_7$ and $R_8$ represent, independently of each other, a hydrogen atom, a linear or branched, substituted or unsubstituted $C_1$-$C_6$ alkyl group, a hydroxyl group, a $C_1$-$C_6$ methoxy group, a cyano group, an amino group or a hydroxycarbonyl or alkoxycarbonyl group;

X represents a hydrogen atom, a monovalent cation.

2. A process according to claim 1, wherein in the compound of formula (I), A is a benzene, anthracene, naphthalene or quinoline nucleus.

3. A process according to claim 1, wherein in the compound of formula (I), A is unsubstituted or substituted with at least one group chosen from a halo radical, a $C_1$-$C_6$ alkyl radical, a $C_1$-$C_6$ alkoxy radical, a $C_1$-$C_6$ alkylsulphonyl radical (-$SO_2$-alkyl), a $C_1$-$C_6$ alkylsulphonate radical (-$SO_3$-alkyl), a cyano radical, a trifluoromethyl radical, a $C_1$-$C_6$ alkylcarbonyl radical, a trifluoromethylsulphonyl radical (-$SO_2$-$CF_3$), a trifluoromethylcarbonyl radical, a phenylsulphonyl radical (-$SO_2$-Ph), a phenylsulphonate radical (-$SO_3$-Ph), a phenylcarbonyl radical, a nitro radical, a $C_1$-$C_6$ alkoxycarbonyl radical, a phosphonyl radical (-$PO(OH)_2$), a phosphonyl($C_1$-$C_6$)alkyl radical (-alkyl-$PO(OH)_2$), a hydroxyl radical, an amino radical, a di($C_1$-$C_6$)alkylamino radical, a (hydroxy($C_1$-$C_6$)alkyl)amino radical, a di(hydroxy ($C_1$-$C_6$)alkyl)amino radical, an (amino($C_1$-$C_6$)alkyl)amino radical, a di(amino($C_1$-$C_6$)alkyl)amino radical, a (hydroxy ($C_1$-$C_6$)alkyl)(($C_1$-$C_6$)alkyl)amino radical, an (amino($C_1$-$C_6$)alkyl)(($C_1$-$C_6$)alkyl)amino radical, an (amino($C_1$-$C_6$) alkyl)(hydroxy($C_1$-$C_6$)alkyl)amino radical, a hydroxy($C_1$-$C_6$)alkyl radical, an amino($C_1$-$C_6$)alkyl radical, a (($C_1$,-$C_6$) alkyl)amino($C_1$-$C_6$)alkyl radical, a di(($C_1$-$C_6$)alkyl)amino ($C_1$-$C_6$)alkyl radical, a (hydroxy($C_1$-$C_6$)alkyl)amino($C_1$-$C_6$) alkyl radical, a di(hydroxy($C_1$-$C_6$)alkyl)amino($C_1$-$C_6$)alkyl radical, an (amino($C_1$-$C_6$)alkyl)amino($C_1$-$C_6$)- alkyl radical, a di(amino($C_1$-$C_6$)alkyl)amino($C_1$-$C_6$)alkyl radical, a (($C_1$-$C_6$)alkyl)-(hydroxy($C_1$-$C_6$)alkyl)amino($C_1$-$C_6$)alkyl radical, an (amino($C_1$-$C_6$)alkyl)(($C_1$-$C_6$)- alkyl)amino radical, a (hydroxy($C_1$-$C_6$)alkyl)(($C_1$-$C_6$)alkyl)amino($C_1$-$C_6$)alkyl radical, a phenyl($C_1$-$C_6$)alkyl radical optionally substituted with at least one substituent chosen from halo, hydroxyl, alkyl, haloalkyl, alkoxy, amino, mono- or dialkylamino, mono- or dihydroxyalkylamino and carboxyl radicals, a cationic group of the quaternary ammonium type, a $C_1$-$C_6$ alkyl radical substituted with a cationic group of the quaternary ammonium type, a carboxyl radical, a ($C_1$-$C_6$)alkyl radical substituted with a carboxyl radical, a thiol radical, a thio($C_1$-$C_6$)alkyl radical, a sulphonate radical (-$SO_3$), a ($C_1$-$C_6$)alkyl radical substituted with a sulphonate radical, a (C$_1$-C$_6$)alkylcarbonyl (C$_1$-C$_6$)alkyl radical, a di(halo(C$_1$-C$_6$)alkyl)amino radical, an acetamido radical, an aryloxy radical, an aryloxy(C$_1$-C$_6$) alkyl radical, an ethenyl radical (-CH=CH$_2$), an ethenylcarbonyl radical (-CO-CH=CH$_2$); two adjacent groups possibly forming an aromatic or heteroaromatic ring, which is unsubstituted or substituted with at least one substituent chosen from halo, hydroxyl, alkyl, haloalkyl, alkoxy, amino, mono- or dialkylamino, mono- or dihydroxyalkylamino and carboxyl radicals, or a ring of -O-C$_m$H$_{2m}$-O- type where m is an integer equal to 1 or 2.

4. A process according to claim 3, wherein in the compound of formula (I), A is unsubstituted or substituted with at least one group chosen from a (C$_1$-C$_6$)alkylsulphonyl radical; a pyridinium or imidazolium group, which is unsubstituted or substituted with at least one substituent chosen from halo, hydroxyl, alkyl, haloalkyl, alkoxy, amino, mono- or dialkylamino, mono- or dihydroxyalkylamino and carboxyl radicals; a tru(C$_1$-C$_6$)alkylammonium group; a sulphonate radical.

5. A process according to claim 1, wherein in the compound of formula (I), X is chosen from a group CR$_1$R$_2$.

6. A process according to claim 1, wherein in the compound of formula (I), R$_1$ and R$_2$ are chosen from a C$_1$-C$_6$ alkyl radical.

7. A process according to claim 1, wherein in the compound of formula (I), R$_3$ is chosen from a hydrogen atom.

8. A process according to claim 1, wherein in the compound of formula (I), W is chosen from a group CR$_4$.

9. A process according to claim 1, wherein in the compound of formula (I), R$_4$ is chosen from a hydrogen atom.

10. A process according to claim 1, wherein in the compound of formula (I), Y is chosen from an oxygen or sulphur atom.

11. A process according to claim 1, wherein in the compound of formula (I), Z is chosen from a group —C$_p$H$_{2p}$—, with p being an integer between 2 and 4, which is unsubstituted or substituted with at least one substituent chosen from halo, hydroxyl, alkyl, haloalkyl, alkoxy, amino, monoalkylamino or dialkylamino, monohydroxyalkylamino or dihydroxyalkylamino and carboxy radicals.

12. A process according to claim 1, wherein in the compound of formula (I), n is equal to 1 or 2.

13. A process according to claim 1, wherein in the compound of formula (I), B is a benzene, carbazole or indole nucleus.

14. A process according to claim 1, wherein in the compound of formula (I), B is unsubstituted or substituted with at least one group chosen from a hydroxyl radical; an amino radical; a di((C$_1$-C$_6$)alkyl)amino radical; a C$_1$-C$_6$ alkyl radical; an acetamido radical; a pyridinium group; a tri(C$_1$-C$_6$) alkylammonium group.

15. A process according to claim 1, wherein the compounds of formula (I) are chosen from the compounds presented in the table below:

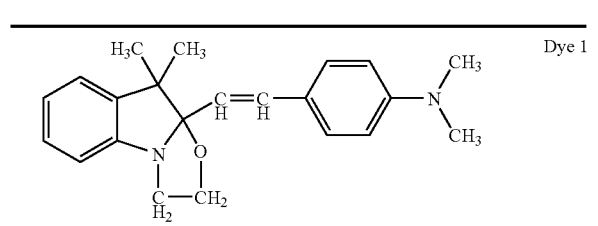

Dye 1

-continued

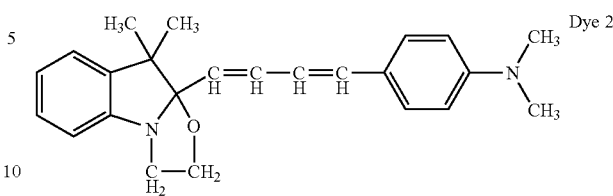

Dye 2

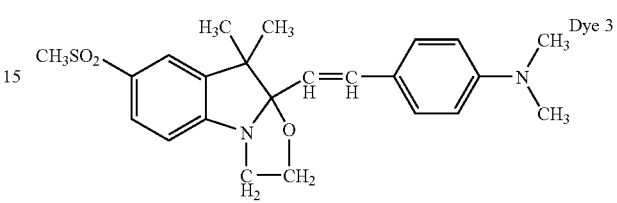

Dye 3

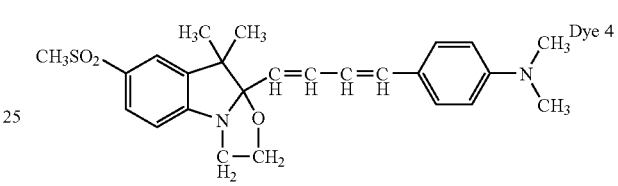

Dye 4

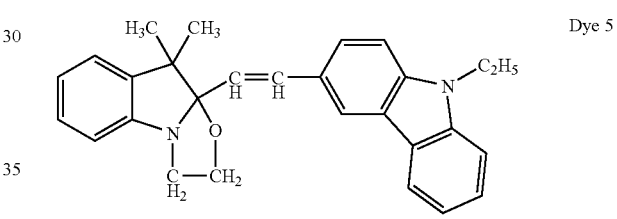

Dye 5

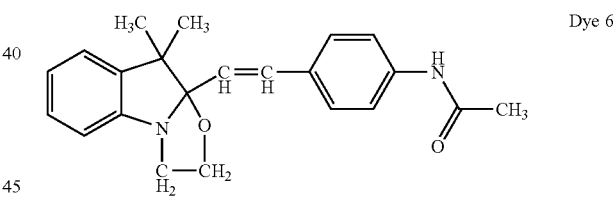

Dye 6

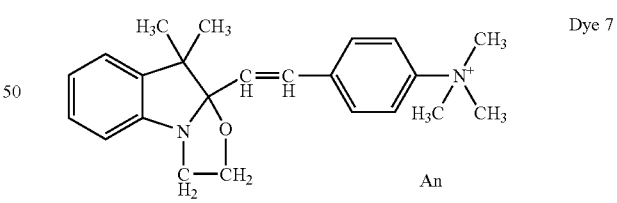

Dye 7

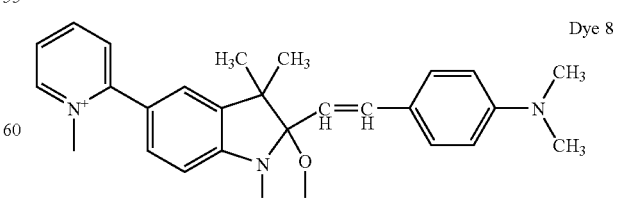

Dye 8

-continued

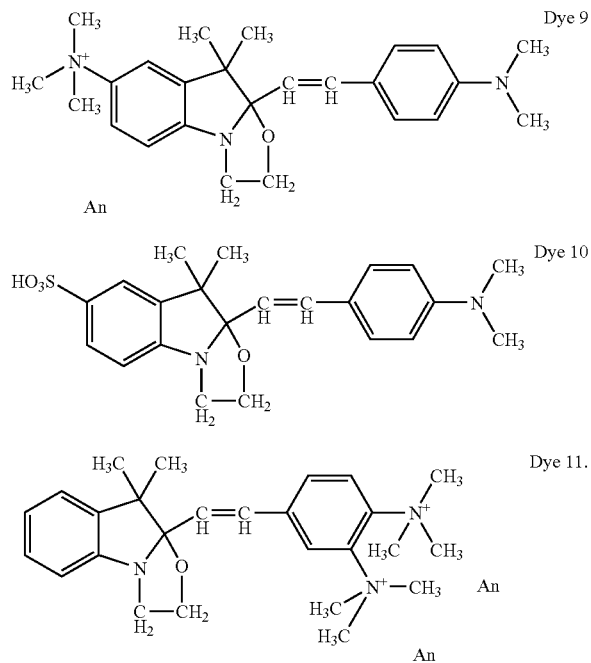

16. A process according to claim 1, wherein the compounds of formula (I) are chosen from 3,3-dimethyl-2-(p-dimethylaminostyryl)indolino[1,2-b]thiazoline; 3,3,5-trimethyl-2-(p-dimethylaminostyryl)indolino[1,2-b]thiazoline; 3,3,5-trimethyl-2-(p- chlorostyryl)indolino[1,2-b]thiazoline; 3,3,5-trimethyl-2-[2-(thienyl)vinyl]indolino[1,2-b-9- thiazoline; 3,3-dimethyl-5-methoxy-2-[2-(9-ethylcarbazolyl)vinyl]indolino[1,2-b]thiazoline; 3,3-dimethyl-5-carboethoxy-2-(p-dimethylaminostyryl)indolino[1,2-b]thiazoline; 3,3-dimethyl-5-chloro-2-[2-(benzothiazolyl)vinyl]indolino[1,2-b]thiazoline; 3,3-dimethyl-5- methoxy-2-(p-dimethylaminostyryl)indolino[1,2-b]thiazoline; 3,3-dimethyl-5-carboethoxy- 2-(3,4-methylenedioxystyryl)indolino[1,2-b]thiazoline; 3,3-dimethyl-5-chloro-2-(p- methylstyryl)indolino[1,2-b]thiazoline; 3,3-dimethyl-5-chloro-2-(p-methoxystyryl]- indolino[1,2-b]thiazoline; 3,3,5-trimethyl-2-(p-acetylaminostyryl)indolino[1,2-b]thiazoline; 3,3-dimethyl-5-methoxy-2-(3-hydroxy-4-methoxystyryl) indolino[1,2-b]thiazoline; 3,3- dimethyl-5-carboethoxy-2-(o-cyanostyryl)indolino[1,2-b]thiazoline; 3,3-dimethyl-5-chloro- 2-(p-dimethylaminostyryl)indolino[1,2-b]thiazoline; 3,3-dimethyl-5-methylsulphonyl-2-(p- dimethylaminostyryl)indolino[1,2-b]thiazoline; 3,3-dimethyl-5-phenylsulphonyl-2-(p- dimethylaminostyryl)indolino[1,2-b]thiazoline; 3,3-dimethyl-5-ethoxycarboxy-2-(p-dimethylaminostyrtyl)indolino[1,2-b]oxazoline.

17. A process according to claim 1, wherein the compounds chosen from the compounds of formula (I), and the addition salts thereof, represents from 0.0001% to 30% by weight relative to the total weight of the dye composition.

18. A process according to claim 1, wherein the dye composition comprises at least one thiol compound comprising at least one thiol function (SH) and a saturated or unsaturated group containing from 1 to 20 carbon atoms, said group being optionally interrupted with at least ono nonadjacent group chosen from -O-, -S-, -S-S-, amino (-NR-), carbonyl (-CO-), oxycarbonyl (-O-CO-), aminocarbonyl (-NR-CO-), aromatic or heteroaromatic nucleus, the amino groups being unsubstituted or substituted with at least one C1-C6 alkyl radical; on condition that the sulphur atom of the thiol function is attached to said group via a carbon atom; said group being optionally substituted with at least one hydroxyl, C1-C6 alkoxy, hydroxycarbonyl, (C1-C6) alkoxycarbonyl, amino, aminocarbonyl or alkylcarbonylamino, in which the amino function is unsubstituted or substituted with at least one C1-C6 alkyl radical.

19. A process according to claim 18, wherein the content of thiol compound ranges from 0.001% to 30% by weight relative to the total weight of the composition.

20. A process according to claim 1, wherein in the compound of formula (II), the aromatic or heteroaromatic nucleus is chosen from benzene, pyridine, quinoline, triazine and indole nuclei; these nuclei being optionally substituted with at least one hydroxyl, C1-C3 alkoxy, hydroxycarbonyl, alkoxycarbonyl with the alkoxy group being C1-C3, amino or cyano groups, and preferably hydroxyl.

21. A process according to claim 20, wherein in the compound of formula (II), the aromatic or heteroaromatic nucleus is chosen from benzene optionally substituted with at least one hydroxyl group.

22. A process according to claim 1, wherein the compound of formula (II) is chosen from gallic acid, 3,5-dihydroxybenzoic acid, p-hydroxybenzoic acid, 2,4-dihydroxybenzoic acid, 3,4-dihydroxybenzoic acid, 2,3-dihydroxybenzoic acid, 2,5-dihydrobenzoic acid and 2,5-dihydroxyphenylacetic acid, salts thereof or precursors thereof.

23. A process according to claim 1, wherein the content of weak acid ranges from 0.001% to 50% by weight relative to the total weight of the dye composition.

24. A process according to claim 1, wherein the dye composition is applied in the presence of at least one oxidizing agent.

* * * * *

UNITED STATES PATENT AND TRADEMARK OFFICE
CERTIFICATE OF CORRECTION

PATENT NO. : 7,527,654 B2  Page 1 of 1
APPLICATION NO. : 11/907525
DATED : May 5, 2009
INVENTOR(S) : Grégory Plos It is certified that error appears in the above-identified patent and that said Letters Patent is hereby corrected as shown below:

On the Title Page, (30) Foreign Application Priority Data should read
-- Oct. 13, 2006  (FR)  0654259 --.

Claim 16, col. 29, line 35, "[1,2-b-9" should read -- [1,2-b] --.

Claim 16, col. 30, lines 3-4, "(p-dimethylaminostyrtyl" should read
-- (p-dimethylaminostyryl --.

Claim 18, col. 30, line 11, "ono" should read -- one --.

Signed and Sealed this

Twenty-third Day of March, 2010

David J. Kappos
*Director of the United States Patent and Trademark Office*